United States Patent [19]
Nicklin et al.

[11] Patent Number: 5,928,859
[45] Date of Patent: Jul. 27, 1999

[54] DETECTION AND BIODEGRADATION OF EXPLOSIVES

[75] Inventors: Stephen Nicklin, Bidborough; Peter Roland Binks, Irby; Neil Charles Bruce, Cambridge; Christopher Edward French, Edinburgh, all of United Kingdom

[73] Assignee: The Secretary of State for Defence in her Britannic Majesty's Government of the United Kingdom of Great Britain & North Ireland of Defence Evaluation & Research Agency, United Kingdom

[21] Appl. No.: 08/983,352

[22] PCT Filed: Jul. 8, 1996

[86] PCT No.: PCT/GB96/01629

§ 371 Date: Feb. 2, 1998

§ 102(e) Date: Feb. 2, 1998

[87] PCT Pub. No.: WO97/03201

PCT Pub. Date: Jan. 30, 1997

Related U.S. Application Data

[30] Foreign Application Priority Data

Jul. 11, 1995 [GB] United Kingdom ............... 9514138
Apr. 4, 1996 [GB] United Kingdom ............... 9607220

[51] Int. Cl.[6] ............... C12Q 1/00; C12N 9/06; B09B 3/00; C07H 21/04
[52] U.S. Cl. ............... 435/4; 435/41; 435/191; 435/252.3; 435/262.5; 435/320.1; 435/822; 536/23.2
[58] Field of Search ............... 435/191, 252.3, 435/320.1, 4, 41, 3.1, 262.5, 822; 536/23.21

[56] References Cited

FOREIGN PATENT DOCUMENTS

| A 0 501 353 | 9/1992 | European Pat. Off. . |
| A 0 511 729 | 11/1992 | European Pat. Off. . |
| WO A 94 21394 | 9/1994 | WIPO . |
| WO A 95 33068 | 12/1995 | WIPO . |

OTHER PUBLICATIONS

Chemical Abstracts, vol. 109, No. 7, Aug. 15, 1988 Columbus, Ohio, US; abstract No. 47787, Posadas Del Rio, Francisco A. et al: "Biotransformation of organic nitrate esters in vitro by human liver, kidney, intestine, and blood serum" XP002018204 see abstract & Drug Metab. Dispos. (1988), 16(3), 477–81 CODEN: DMDSAI;ISSN: 0090–9556.

Chemical Abstracts, vol. 125, No. 3, Jul. 15, 1996 Columbus, Ohio, US; abstract No. 27992, Binks, Peter R. et al: "Degradation of pentaerythritol tetranitrate by Enterobacter cloacae PB2" XP002018205 see abstract & Appl. Environ. Microbiol. (1996), 62(4), 1214–19 CODEN: AEMIDF;ISSN: 0099–2240.

*Primary Examiner*—Robert A. Wax
*Assistant Examiner*—Elizabeth Slobodyansky
*Attorney, Agent, or Firm*—Nixon & Vanderhye

[57] ABSTRACT

An enzyme capable of catalyzing the removal of nitrite from pentaerythritol tetranitrate (PETN) is provided. The enzyme (known as PETN reductase enzyme) is produced by culturing a novel strain of the *Enterobacter cloacae* bacterium isolated from nature. The strain designated PB2 has been deposited as NCIMB 40718. The amino acid sequence of the enzyme and the genetic sequence which encodes for this enzyme have also been determined. A PETN reductase enzyme encoded by the on gene is provided. A method for producing PETN reductase enzyme in large quantities and methods of bioremediation using the enzyme so produced are also provided. Additionally there is provided a method of detecting the presence of PETN in a sample together with a biosensor for use in such a method.

29 Claims, 5 Drawing Sheets

```
NcoI(-279)
ccatggataa aggagccagc ggcgtgattg ccctgttggc tcaggcgctg  -230 gagagcgggc gcaatgaaaa aacgctctcc ttctccggcg atccgctcac  -180 gcaggcacag gtgctctatt ccctctggtt aggcgccaac ctgcaagcaa  -130 aaatgtctcg cagcgccgtg ccgctcgaaa gcgcgctggc gcatgtgaaa  -80 aactgtatta ccgcgcctgg cgtgtagccg gcgtttttat ttacccttt   -30
      SalI(-25)              rbs
actagtcgac tggtctactc aggagccgtt atgtccgctg aaaagctgtt  +20
                                  M  S  A  E  K  L  F tacccactg aaagtgggtg ccgttactgc cccaaaccgc gtgtttatgg   +70
 T  P  L  K  V  G  A  V  T  A  P  N  R  V  F  M
                                     EcoRV(106)
ccccacttac ccgtctcgc agcatcgagc cgggcgatat cccaacgcca   +120
 A  P  L  T  R  L  R  S  I  E  P  G  D  I  P  T  P ttgatgggtg agtattaccg ccagcgcgcc agcgcgggcc tgattatctc   +170
 L  M  G  E  Y  Y  R  Q  R  A  S  A  G  L  I  I  S cgaagccacg cagatttctg ctcaggcaaa aggctacgcc ggtgcaccgg   +220
 E  A  T  Q  I  S  A  Q  A  K  G  Y  A  G  A  P gtctgcacag cccggaacag atcgccgcgt ggaaaaaaat caccgcaggc   +270
 G  L  H  S  P  E  Q  I  A  A  W  K  K  I  T  A  G gtgcatgctg aagatggccg tattgcggtt cagctgtggc acaccggtcg   +320
 V  H  A  E  D  G  R  I  A  V  Q  L  W  H  T  G  R tatctcacac agcagcatcc agcctggcgg tcaggcgccg gtttctgcct   +370
 I  S  H  S  S  I  Q  P  G  G  Q  A  P  V  S  A ctgccctgaa cgccaatacc cgcacttccc tgcgcgatga aaacggtaat   +420
 S  A  L  N  A  N  T  R  T  S  L  R  D  E  N  G  N
       SalI(430)
gcgatccgcg tcgacaccac cacgccacgc gcgctggagc tggacgagat   +470
 A  I  R  V  D  T  T  T  P  R  A  L  E  L  D  E  I
SmaI(471)                                     SmaI(512)
cccgggtatc gtgaatgatt tccgtcaggc cgtcgccaac gcccgggaag   +520
 P  G  I  V  N  D  F  R  Q  A  V  A  N  A  R  E
```

Fig.3-2.

```
                                                BstEII(556)
cgggcttcga cctggttgag cttcactctg cgcacggtta cctgctgcat +570
 A  G  F  D  L  V  E  L  H  S  A  H  G  Y  L  L  H cagttcctgt ccccgtcttc caaccagcgt accgaccagt acggcggcag +620
 Q  F  L  S  P  S  S  N  Q  R  T  D  Q  Y  G  G  S cgttgaaaac cgcgcgcgtc tggtgcttga agtggtggat gctgtctgta +670
  V  E  N  R  A  R  L  V  L  E  V  V  D  A  V  C atgagtggag cgcagaccgc attggtattc gtgtctcccc gatcggtact +720
 N  E  W  S  A  D  R  I  G  I  R  V  S  P  I  G  T SalI(730)
ttccagaacg tcgacaacgg tccgaacgaa gaagcagacg cgctgtatct +770
 F  Q  N  V  D  N  G  P  N  E  E  A  D  A  L  Y  L gattgaagag ctggcgaaac gcggtatcgc ctatctgcac atgtccgaga +820
  I  E  E  L  A  K  R  G  I  A  Y  L  H  M  S  E cggacttggc aggcggcaag ccttacagtg aagccttccg tcagaaagtg +870
 T  D  L  A  G  G  K  P  Y  S  E  A  F  R  Q  K  V cgcgagcgct tccacggcgt gattatcggg gcgggtgcgt atacggcaga +920
 R  E  R  F  H  G  V  I  I  G  A  G  A  Y  T  A  E StuI(945)
aaaagccgag gatttgatcg gtaaaggcct gatcgacgcc gtggcctttg +970
 K  A  E  D  L  I  G  K  G  L  I  D  A  V  A  F gccgtgacta cattgctaac ccggatctgg ttgcccgttt gcagaaaaaa +1020
 G  R  D  Y  I  A  N  P  D  L  V  A  R  L  Q  K  K HindIII(1047)
gccgaactga acccgcagcg tcctgaaagc ttctatggcg gcggcgcgga +1070
 A  E  L  N  P  Q  R  P  E  S  F  Y  G  G  G  A  E aggttatacc gactacccct cactgtaatc ccgctttgta cattgatagc +1120
 G  Y  T  D  Y  P  S  L  * ggcgaccttt cgccgctata ctaaaacatc gtttctgttc aaaaagataa +1170 tccattcgac tggttaatga ggaaattatg cgcctacttc acaccatgct +1220
                         ClaI(1246)
gcgcgttggc gacctgcaac gttccatcga t
```

Fig.4.

SAEKLFTPLKVGAVTAPNRVFMAPLTRLRSIEPGDIPTPLM

GEYYRQRASAGLIISEATQISAQAKGYAGAPGLHSPEQIA

AWKKITAGVHAEDGRIAVQLWHTGRISHSSIQPGGQAPVS

ASALNANTRTSLRDENGNAIRVDTTTPRALELDEIPGIVN

DFRQAVANAREAGFDLVELHSAHGYLLHQFLSPSSNQRTD

QYGGSVENRARLVLEVVDAVCNEWSADRIGIRVSPIGTFQ

NVDNGPNEEADALYLIEELAKRGIAYLHMSETDLAGGKP

YSEAFRQKVRERFHGVIIGAGAYTAEKAEDLIGKGLIDAV

AFGRDYIANPDLVARLQKKAELNPQRPESFYGGGAEGYT

DYPSL

Fig.5.

DETECTION AND BIODEGRADATION OF EXPLOSIVES

This invention relates to the field of explosives detection and biodegradation and in particular to a novel enzyme, to the amino acid sequence for the enzyme, to the gene which encodes the enzyme and to methods of producing the enzyme recombinantly. The invention further relates to a method of using the enzyme to catalyze the aerobic biodegradation of pentaerythritol tetranitrate (hereinafter referred to by the commonly used abbreviation PETN) and to a method and apparatus for the detection of PETN using the enzyme.

The novel enzyme of this invention has also been demonstrated to liberate nitrite from glycerol trinitrate (GTN) and from ethylene glycol dinitrate (EGDN) which are further examples of nitrate ester species. The enzyme is referred to as a PETN reductase.

Nitrate esters, though apparently extremely rare in nature, are produced in significant quantities by the chemical industry and comprise, for example, an important class of energetic materials having applicability as explosives and propellants. PETN itself has a diverse range of applications including as an explosive in blasting caps and detonators and in pharmaceutical compositions as the active ingredient of long-acting, slow onset coronary vasodilators for the prevention of angina attacks. The manufacture, handling and disposal of PETN can all lead to the contamination of the environment with PETN. There are concerns regarding the environmental fate of nitrate esters due to their relative recalcitrance and there therefore exists a need for a means of removing such contaminants from the environment without producing other undesirable pollutants. There is also an urgent requirement for a better method of detecting PETN as the currently proposed analytical systems rely mostly on use of bulky and sophisticated pieces of equipment such as gas chromatograms or mass spectrometers and/or require specially trained laboratory technicians for their application.

It is an aim of this invention to provide an enzyme which is capable of catalyzing the biodegradation of PETN and which may be employed in a bioremediation system for the environmental decontamination of the PETN pollutant. It is a further aim to provide an enzyme which is useful for PETN detection systems.

Figure 4:
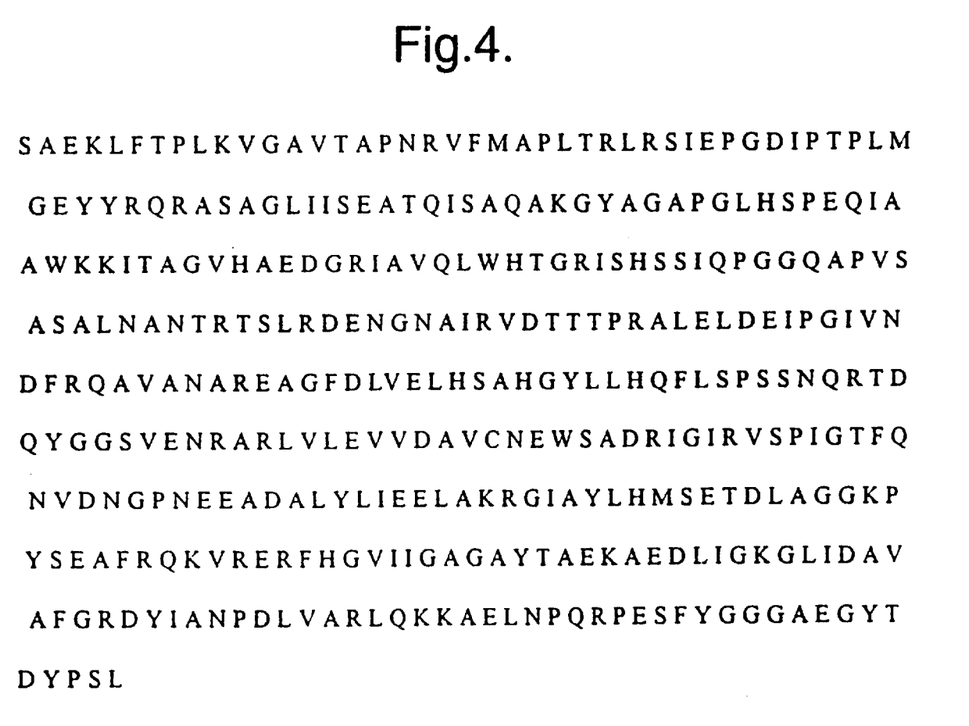
FIG. 4 sets out the amino acid sequence (SEQ ID NO: 2) per se.

According to a first aspect of the present invention therefore, there is provided a PETN reductase enzyme which catalyses the removal of nitrite from PETN characterised in having the amino acid sequence shown in FIG. 4 or a derivative thereof By derivative herein is meant a version of the enzyme sequence of FIG. 4 containing insertions, deletions and/or substitutions of the amino acid sequence such that the functionality of the enzyme is retained.

Based on the evidence of the amino acid sequence it is possible to state that the enzyme is a member of the family of α/β-barrel flavoprotein oxidoreductases.

This PETN reductase enzyme has the characteristics that, in the presence of nicotinamide adenine dinucleotide phosphate (NADPH hereinafter), it:

1) catalyses the removal of nitrite from PETN; and 2) has reductase activity specifically at the nitrate ester linkage of PETN.

The enzyme further has a pH optimum of 6.5 and has a $M_r$ of about 40,000 Daltons as determined by gel filtration. The subunit $M_r$, as estimated by SDS-PAGE (polyacrylamide gel electrophoresis), was also 40 000. These results suggest that PETN reductase is a monomer of $M_r$ approximately 40,000.

The PETN reductase enzyme of this invention may be further identified by additional characteristics such as its pH optimum, catalytic activity, thermal stability or molecular weight. Details of such further characteristics are given in Example 3 below but it must be stressed that these characteristics are variable to a degree depending upon the conditions under which the microorganism producing the enzyme is grown and upon the degree of purification of the crude product. Variations of this kind will be well understood by those skilled in the art.

The purified enzyme is visibly yellow and shows a visible absorption spectrum characteristic of an oxidised flavoprotein. The flavin was liberated from PETN reductase by boiling followed by removal of denatured protein by centifugation, indicating that the flavin is not covalently bound. In two thin layer chromatography systems the liberated flavin comigrated with authentic flavin mononucleotide (FMN) and not with flavin adenine dinucleotide (FAD). Flavin standards subjected to the protocol used to liberate the flavin from PETN reductase showed no change; in particular, FAD was not hydrolysed to FMN. These results indicate therefore that the enzyme is a monomeric flavoprotein which binds FMN non-covalently.

In a second aspect, the present invention provides the gene (designated onr (for organic nitrate ester reductase)) which encodes the PETN reductase enzyme or a derivative thereof By derivative of the gene is meant herein homologues of the gene having a coding sequence which is at least 70% identical to the onr gene, involving any and all single or multiple nucleotide additions, deletions and/or substitutions thereto. The nucleotide sequence of the onr gene as determined herein is set out in FIG. 3.

According to a third aspect of the invention there is provided a recombinant DNA molecule including the nucleotide sequence of the onr gene or a nucleotide sequence which is at least 70% identical to the nucleotide sequence of the onr gene.

In a further aspect the present invention provides the PETN reductase enzyme which is encoded by the onr gene.

It will be readily apparent to those skilled in the art that once the sequence of the genetic material which encodes for PETN reductase enzyme in the *E. cloacae* PB2 microorganism has been identified in accordance with this present invention, it will be possible according to well known techniques to transform a suitable host cell with the onr gene (or a derivative thereof) such that the host cell produces (expresses) the recombinant gene product ie. PETN reductase. This may be done by any suitable method such as splicing the gene into a vector and transforming said host cell with that vector.

Accordingly the present invention therefore also provides a recombinant DNA vector containing the onr gene or a derivative thereof and a host cell transformed with the onr gene or a derivative thereof This transformation may be performed using such a vector.

The manner in which such vectors and recombinant DNA may be produced will be readily apparent to those skilled in the art given that the methods applicable, including the choice of a suitable host cell and of suitable promoters are generally well understood in the field.

Among host cells which might be used for the purpose, it may be appropriate to use *E cloacae* PB2 cells transformed with additional copies of the onr gene.

Using the host cell transformed with the onr gene or a derivative thereof and spliced behind a suitable promoter of the host cell, it will be possible to generate PETN reductase enzyme in industrially useful quantities, again by techniques which are well known in the art. There is also provided therefore, a method for the production of PETN reductase enzyme or a derivative thereof which comprises the steps of:

transforming a host cell with the onr gene or a derivative thereof, growing the host cell under conditions appropriate for expression of the said onr gene product, and extracting the onr gene product from the growing medium or from the host cells after disruption thereof.

Most conveniently the production process is run in a continuous or semi-continuous manner to continuously extract the enzyme produced from the growth medium for the host cell, employing techniques which are well understood in the art. If the host cell produces the enzyme intracellularly, disruption of the cells in the culture will be necessary to extract the enzyme product. Suitable host cells may be provided by either prokaryotic or eukaryotic organisms. A PETN reductase enzyme produced according to the above methods is provided as a further aspect of the present invention.

The action of the novel reductase enzyme of the present invention is to catalyze the reduction of PETN into pentaerythritol tri- and di-nitrates by attack at the nitrate ester linkage of PETN. The ability to specifically attack the nitrate ester linkage of PETN is a distinctive feature of this PETN reductase enzyme that is not possessed by commercially available reductases. A description of the mode of identification of the reaction products of PETN is set out in Example 2 below.

The ability of the novel PETN reductase enzyme to catalyse the removal of nitrite from PETN in the presence of NADPH allows the enzyme to be used in the detection of PETN. According to a yet further aspect of the invention therefore, there is provided a method of detecting the presence of PETN in a sample which comprises subjecting the sample to the PETN reductase enzyme of this invention in the presence of NADPH and under conditions to permit reaction of any PETN present in the sample and detecting the occurrence of such reaction. Conveniently, detection of the reaction would be by means of a bioluminescence test using either bacterial or firefly luciferase, or by a calorimetric or amperometric method as is well known in the art.

In a further aspect, therefore, the present invention also provides a biosensor for the detection of PETN in a sample which comprises means for contacting the sample with a PETN reductase enzyme in the presence of NADPH and means for detecting the occurrence of a reaction, catalyzed by the enzyme, of PETN when PETN is present in the sample. The means for detecting the occurrence of a reaction may conveniently comprise a bioluminescent transducer or an amperometric transducer. Such sensors can be used as the basis for highly convenient portable detectors for checking luggage, clothing etc. for traces of PETN.

The methods of making biosensors that rely on amperometric or bioluminescent changes in the test reaction are well known in the art. For example, UK Patent Application Publication No. 2,231,332A (NRDC) describes such methods and their use in biosensors, the contents of which in relation thereof is hereby incorporated by reference. Any of such methods may be of use in detecting the occurrence of the PETN degrading reaction and hence in the detection of PETN.

Typically, in the case of a bioluminescent biosensor, luciferase is used. This enzyme is responsible for the light-emitting reaction of luminous bacteria and catalyzes the reaction of molecular oxygen with reduced flavin and aliphatic aldehyde to form long-lived intermediates whose slow breakdown provides energy to give light emission with reasonably high quantum yield. In coupling the PETN reductase to such a bioluminescent system, the $NADP^-$ generated through the activity of the PETN reductase is detected by the oxidation of an alcohol such as decanol, octanol or hexanol, to its corresponding aldehyde in the presence of an alcohol dehydrogenase. The aldehyde is then detected by reaction with reduced flavin ($FMNH_2$) in the presence of oxygen together with luciferase to catalyse the reaction. The intensity of the emitted light provides a measure of the NADPH converted to NADPH which in turn provides a measure of the PETN concentration present.

It is anticipated that using such a scheme, sensitivity to PETN will be in the range 0.1 nmol–0.1 $\mu$mol.

A convenient colorimetic detection procedure uses a Griess reagent which generates a characteristic purple colouration in the presence of nitrite. A standard curve showing the relationship of absorbance at 540 nm with PETN concentration in soil samples can be generated by carrying out tests using a series of soil samples containing known concentrations of PETN. This standard curve can then be used to determine the concentration of PETN in unknown test soil samples. (Further details of a colorimetric detection method are given in Example 7).

In an amperometric biosensor, the NADPH generated by reaction of the PETN reductase in the presence of NADPH may be re-reduced enzymatically with L-glutamate dehydrogenase (eg. from bovine liver), glutamate-pyruvate transaminase (eg. from pig heart) and pyruvate oxidase (eg. from Pediococcus sp.). The product is hydrogen peroxide and the concentration of this substance may be directly measured, as, for example, on a platinum electrode at 0.7 v. or via a mediatorless peroxidase electrode.

It has been found that PETN reductase will also liberate nitrite from glycerol trinitrate (GTN) and from ethylene glycol dinitrate (EGDN) in addition to PETN. The apparent $K_m$ for GTN in 50 mM phosphate buffer, pH 7.0, in the presence of 0.2 mM NADPH, was measured using GTN concentrations between 5 $\mu$M and 200 $\mu$M and was found to be 22+2 $\mu$M (one standard error). The initial product of GTN denitration has not yet been determined.

The apparent $K_m$ for EGDN was measured with EGDN concentrations between 0.5 and 2.5 mM and was found to be approximately 2 mM. In conjunction with the observation that pentaerythritol dinitrate does not appear to be a substrate for this enzyme, this suggests that two nitrate groups in addition to that being reduced may be required for good binding or activity. The value of $K_m$ for PETN could not be determined due to the poor solubility of this substrate. Accordingly in addition to its use in equipments for detecting PETN, the PETN reductase enzyme may be used for the purpose of remediation of environments contaminated with PETN, GTN and/or EGDN. Such environments may be either sites where these materials have been historically produced or in the context of the treatment of by-product streams etc associated with current manufacturing and handling areas for these materials.

In particular therefore, there is provided according to a further aspect of this present invention a method for the bioremedial treatment of an environment contaminated with PETN, GTN or EGDN, which method comprises the steps of adding to the contaminated environment a quantity of PETN reductase enzyme and maintaining the mixture under conditions appropriate for degradation of PETN, GTN and/or EGDN by the enzyme such that the PETN, GTN and/or EGDN present in the material is consumed.

The material concerned may be, for example, a waste stream of material containing PETN originating from the destruction of an explosives charge containing PETN or a sample of PETN-contaminated earth or other material. In the former case bioremedial treatment may be conveniently carried out in a reactor vessel, whereas in the latter instance the enzyme may be introduced directly into the material by adding the enzyme to it. Other appropriate methods of effecting treatment will be readily apparent to those skilled in the art.

The PETN reductase enzyme of the present invention is obtained from a bacterial strain isolated from nature. The bacterial strain is a strain of *Enterobacter cloacae* herein designated PB2. This novel bacterial isolate forms a further aspect of the present invention. A sample of the novel isolate has been deposited under the terms of the Budapest Treaty on the International Recognition of the Deposit of Microorganisms for the purpose of patent procedures at the UK National Collection of Industrial and Marine Bacteria, 23 St Machar Drive, Aberdeen AB2 1RY, Scotland on the Apr. 14, 1995 under deposit number NCIB 40718.

According to a yet further aspect of the present invention therefore, the ability of the PETN reductase enzyme to degrade PETN as described above provides an alternative method for the bioremedial treatment of a PETN-contaminated environment which method comprises the step of inoculating the environment with a sample of the bacterial isolate of *Enterobacter cloacae* designated PB2 and allowing the isolate to consume the PETN present in the environment. The environment concerned may be, for example, a waste stream of material containing PETN originating from the destruction of an explosives charge containing PETN or a sample of PETN-contaminated earth or other material. In the former case bioremedial treatment may be conveniently carried out in a reactor vessel, whereas in the latter instance the isolate may be introduced directly into the environment by inoculating the contaminated soil with it. Other appropriate methods of effecting treatment will be readily apparent to those skilled in the art.

The bacterium identified above will only produce the enzymic activity to which the present invention refers when it is cultured on PETN as the nitrogen source. Further characteristics of the deposited bacterium PB2 are listed below.

| | |
|---|---|
| Gram stain | -ve |
| Spores | -ve |
| Motility | +ve |
| Growth | |
| 37° C. | +ve |
| 41° C. | +ve |
| 45° C. | +ve |
| Catalase | +ve |
| Oxidase | -ve |
| Fermentative in glucose OF | +ve |
| Colony morphology: | Round, regular, entire, smooth, glossy cream, low convex, semi-translucent, 1 mm in diameter. |
| Rapid Test (API): 24 hours at 30° C. | |
| β galactosidase | + |
| Arginine dihydrolase | + |
| Lysine decarboxylase | - |
| Ornithine decarboxylase | + |
| Citrate utilisation | + |
| H$_2$S production | - |
| Urease | - |
| Tryptophan deaminase | - |
| Indole production | - |
| Voges Proskauer | + |
| Gelatinase | - |
| Acid production from:- | |
| Glucose | + |
| Mannitol | + |
| Inositol | - |
| Sorbitol | + |
| Rhamnose | + |
| Sucrose | + |
| Melibiose | + |
| Amygdalin | + |
| L (+) Arabinose | + |
| Cytochrome oxidase | - |
| Further Tests, 30° C., 7 days | |
| Methyl Red (37° C.) | - |
| Acid from Raffinose | + |
| Acid from α-Methyl-glucoside | + |
| Acid from Adonitol | + |
| Gelatin | + |

PETN reductase can be produced by culturing *E. cloacae* on PETN as a nitrogen source. When grown on NH$_4$NO$_3$ the activity can be induced by the addition of PETN. However, this is not the case when grown on NH$_4$Cl. Cultivation is preferably anoxic at any usual temperature, eg within 20 to 40° C. range, preferably 25 to 30° C. To obtain PETN reductase the cells can be disrupted in any conventional way. Preferably, a cell free extract is made. The enzyme is then recovered from the extract.

Instead of the precise starting organism deposited, a mutant thereof, eg derived by gamma-ray irradiation or the use of a chemical mutant, induction by culture on another medium etc. or a transconjugant thereof with another bacterium or an artificially produced variant can be used. The ability of any such organism to give the enzymic activity can be readily determined by the skilled person.

In a further manner of use of the previously described activity of the PETN reductase of this invention, there is provided a method for producing pentaerythritol di- and tri-nitrates which may have useful pharmaceutical activity (biotransformation) by reacting PETN with the PETN reductase enzyme of the present invention, in the presence of NADPH.

The invention will now be further described with reference to the following figures of which:

FIG. 3 shows the nucleotide sequence of onr and the deduced amino acid sequence of PETN reductase (SEQ ID NO: 1 and SEQ ID NO: 2, respectively);

EXAMPLE 1

Preparation of the enzyme activity from the bacterial strain *Enterobacter cloaca* PB2

1. Materials and Methods

*Enterobacter cloacae* PB2 was isolated using techniques standard in the art, from samples collected from a natural source by enrichment with PETN as the nitrogen source.

*E. cloacae* was grown in 1 liter of defined medium consisting of 10 mM potassium phosphate buffer, pH 7.3, containing 0.25 mM MgSO$_4$, 5 mM glucose, 5 mM succinate, 10 mM glycerol, 2 mM $NH_4NO_3$, PETN (10 mM) and trace elements (as described by Pfennig and Lippert, Arch. Microbiology. 1966, 55, 726–739.) supplemented with $CaCl_2.2H_2O$ (100 mg/l).

Flasks were incubated at 180 r.p.m in a shaking incubator at 30° C. For bulk preparation of bacteria, 1 liter of seed culture was aseptically added to a 75 liter culture vessel, containing 50 liters of sterile medium. The bulk cultures were incubated at 30° C., stirred at 150 r.p.m. with sterile aeration to maintain dissolved oxygen at 10% saturation.

Cell free extracts were prepared from cells grown in the above manner. Cells were harvested from a 75 liter bulk culture, using continuous flow centrifugation (Sorval TZ-28 rotor, Sorval RC-5C centrifuge). Those obtained from a smaller volume culture were then pelleted by spinning at 10,000 g for 15 min at 4° C. in a Sorval RC-SC centrifuge fitted with a GS-3 rotor. These pelleted cells were resuspended in 2 ml of bis-Tris propane buffer (pH 7), per gram wet cell weight. Cells were disrupted by sonication in an MSE Soniprep (Fisons, Instruments, FSA Ltd.) using 6×12 $\mu$m bursts of 15 seconds, alternated with 30 seconds of cooling in melted ice. Cell debris and unbroken cells were removed by centrifugation at 20,000 g for 20 min at 4° C. in a Sorval RC-5C centrifuge using a SS-34 rotor, to give clarified cell free extract.

2 Chemicals

PETN was of the highest purity and other chemicals were of analytical grade, and unless stated otherwise, were obtained from BDH Ltd. (Poole, U.K), Sigma Chemical Company Ltd. (Poole, U.K) or Aldrich (Gillingham, U.K).

3 Assays

PETN reductase

PETN reductase activity was determined by monitoring the disappearance of PETN by HPLC in 50 mM bis-Tris propane buffer (pH 7), containing PETN (47 $\mu$M, final concentration), 40 $\mu$l enzyme and NADPH (0.2 mM, final concentration) in a final volume of 1 ml.

Alternatively, PETN degradation was also followed by monitoring the release of nitrite using Greiss reagent (Rosenblatt, Burrows, Mitchell and Parmer. 1991: "Organic Explosives and Related Compounds" in The Handbook of Environmental Chemistry 3 (G), edited by O. Hutzinger, Springer-Verlag). The assay was carried out as described above and terminated by the addition of ferricyanide (0.5 mM, final concentration) and phenazine methosulphate (0.2 mM, final concentration). Sulphanilic acid (0.6 mM, final concentration) was added and left to stand for 15 min. N-1-naphthylethylenediamine (0.4 mM, final concentration) was then added and after 5 min the colour which developed was measured spectrophotometrically at 540 nm. The unit enzyme activity is defined as the amount of enzyme necessary to release 1 $\mu$mol of nitrite per min at 30° C.

The degradation of PETN could also be determined by monitoring the oxidation of NADPH at 340 nm.

Protein

Protein was routinely assayed by the Coomassie dye-binding method of Bradford (Anal. Biochem. (1976) 72, 248–254) using commercially available reagent and Bovine Serum Albumin standard (Pierce Ltd.- obtained through Life Science Labs Ltd., Luton). An aliquate (20 $\mu$l) of sample containing 0.2–1 mg protein/ml was added to I ml of reagent and the reaction allowed to develop for 5 min at room temperature prior to reading the absorbance at 595 nm against a blank of buffer (20 $\mu$l) plus reagent (I ml). Comparison to a standard curve of standard values (0–1 mg/ml) allowed calculation of the protein concentration in the sample.

Gel filtration standards

The following enzymes were used as molecular weight markers in gel filtration experiments: Bovine Serum albumin, Ovalbumin, Chymotrypsin and Ribonuclease A (molecular weights 67,000, 43,000, 25,000, 13,700 Daltons respectively).

EXAMPLE 2

Purification of PETN reductase

To the crude extract, obtained from 30 g wet weight cells, enough ammonium sulphate was added to achieve 50%. saturation. After stirring at 4° C. for 5 min the resulting precipitate was removed by centrifugation at 20,000 g for 20 min. Ammonium sulphate was added to the resulting supenatent to achieve 90% saturation. The resulting precipitate was collected by centrifugation at 4° C. and redissolved in 4 ml of 50 mM bis-Tris propane buffer (pH 7). The sample was desalted using a PD-10 column packed with Sephadex G-25M (Pharmacia) and concentrated to 8 ml by ultrafiltration using an Amicon stirred ultrafiltration chamber equipped with a Diaflo type YM-3 membrane filter that retained proteins with molecular weights greater than 3,000 Daltons. The fast protein liquid chromatography (FPLC) system was used in combination with a Q-sepharose column to further purify the sample. The FPLC system consisted of two LKB P500 pumps (Pharmacia) combined with a model LCC-500 PLUS gradient controller (Pharmacia), a Rheodyne injection valve, a single path TV monitor (Pharmacia) and an LKB 2212 HELIRAC fraction collector. FPLC was carried out at room temperature, but the fractions collected were cooled on ice. The concentrate was applied to the Q-sepharose column (1×7 cm) which had previously been equilibrated with 50 mM bis-Tris propane (pH 8.5) at room temperature. The column, was washed extensively with buffer until no further absorbance at 280 nm was detected in the eluent, whence the reductase was eluted with 10 mM NaCl. Fractions (14 ml) were collected at a flow rate of 1 ml/min, desalted and concentrated by ultrafiltration as previously described. The sample was then applied to a Mimetic Orange 2 affinity chromatography column (8×20 mm, Affinity Chromatography Ltd.) that had previously been equilibrated with 50 mM bis-Tris propane (pH 7) at 4° C. The column was washed with 2 column volumes of buffer. The third column volume contained the reductase activity which was collected.

Results

The specific activity of the PETN reductase was measured after the various stages of purification described above. The resulting data is set out in Table 1, from which it may be seen that in a cell free extract of E cloacae PB2 grown on PETN as a nitrogen source, PETN reductase was present at a specific activity of 0.025 unit/mg protein while ultimately it was purified 182 fold.

TABLE I

| Purification step | Volume (ml) | Total protein (mg) | Total activity (units) | Specific activity (units/mg) | Recovery of activity (%) | Purification factor (-fold) |
|---|---|---|---|---|---|---|
| Crude extract | 40 | 361.6 | 9.04 | 0.025 | 100 | — |
| Ammonium sulphate fractionation | 8 | 31.4 | 3.47 | 0.110 | 39 | 4 |
| Q-Sepharose ion exchange chromatography | 10.5 | 15 | 0.83 | 0.720 | 9 | 29 |
| Mimetic Orange 2 affinity chromatography | 16 | 0.16 | 0.728 | 4.550 | 8 | 182 |

EXAMPLE 3

Characteristics of PETN reductase pH optimum

Purified PETN reductase (50 μl, 0.5 μg protein) was incubated for 4 min at 30° C. Kith 47 μM PETN in a range of buffers: 50 mM bis-Tris propane (pH 6.5, 7, 7.5 and 8), 50 mM 2-[N-morpholino)ethanesulphonic acid (MES) (pH 5.5, 6, 6.5) and 50 mM bis-Tris (pH 6.2, 6.3, 6.4, 6.5, 6.6, 6.7 and 6.8). The concentration of nitrite was then measured using Greiss reagent.

PETN reductase displayed a pH optimum of 6.5.

$K_m$ of enzyme

The $K_m$ of PETN reductase was above the maximum solubility of PETN (47μM)

Molecular weight determination

The molecular weight of the native enzyme was determined by the method of Andrews (Biochem. J. (1964) 91, 222–223). Measurements were carried out on a Superose 6 HR 10/30 column (1×30 cm). Purified PETN reductase (10 μg) was mixed with marker proteins and added to the column. The column was eluted with bis-Tris propane buffer (pH 7) and 0.4 ml fractions collected. The elution volume of PETN reductase corresponded to a molecular weight of 40,000 Daltons.

Molecular weight determination was also performed using SDS-PAGE. The purified PETN reductase ran as a distinct major band corresponding to a molecular weight of 42,000 Daltons. This similar value to that of the native enzyme implies that any effect of detergent/protein interactions in determining the molecular weight of the enzyme were minimal.

EXAMPLE 4

Cloning and sequencing of the structural gene onr encoding PETN reductase.

The structural gene encoding PETN reductase, designated onr (for organic nitrate ester reductase) was cloned by the use of degenerate oligonucleotide probes based on the N-terminal amino acid sequence of the purified protein.

To obtain the N-terminal amino acid sequence of PETN reductase, purified enzyme (4.0 μg) was transferred from an SDS/polyacrylamide gel to a poly(vinylidene difluoride) membrane (ProBlott; Applied Biosystems, Foster City, Calif., USA) using the Pharmacia PhastTransfer semi-dry blotting apparatus (Pharmacia Biotech, St. Albans, UK). The transfer buffer consisted of 25 mM tris(hydroxymethyl) aminomethane, 190 mM glycine, 10% W/V methanol. Transfer was with a current of 25 mA for 30 min. The N-terminal amino acid sequence was determined by automated Edman degradation by the Protein and Nucleic Acid Chemistry Facility, Cambridge Centre for Molecular Recognition, Department of Biochemistry, University of Cambridge.

Based on elements of the amino acid sequence, the following oligonucleotide probes were designed:

1) ACTTT(G/C)AG(G/C)GG(G/C)GTGAA(G/C)AGTTTTC(G/C)GC (SEQ ID NO: 3)

2) GT(G/C)AG(G/C)GG(GC)GCCATGAA(G/C)AC(G/C)CGGTT (SEQ ID NO: 4)

Oligonucleotides were synthesized by the Protein and Nucleic Acid Chemistry Facility, Cambridge Centre for Molecular Recognition, Department of Biochemistry, University of Cambridge. Genomic DNA was prepared from E cloacae PB2 as described by Ausubel et al. (Ausubel, F. M., Brent, R., Kingston, R. E. et al. (1994) Current Protocols in Molecular Biology, John Wiley and Sons, New York). Genomic DNA was digested to completion with various combinations of restriction endonucleases obtained from Boehringer-Mannheim (Lewes, E. Sussex, UK), Gibco/BRL (Paisley, Scotland, UK) and Promega (Southampton, Hants., UK). DNA fragments were separated by agarose gel electrophoresis using 0.8% (w/v) agarose gels and TAE buffer (Sambrook, J., Fritsch, E. F. and Maniatis, T. (1989) Molecular Cloning: A Laboratory Manual, 2nd edn., Cold Spring Harbor Laboratory Press, Cold Spring Harbor, New York), and transferred to nylon membranes (Hybond N+, Amersham, Little Chalfont, Bucks., UK) by alkaline capillary blotting according to the manufacturer's protocol.

The oligonucleotide probes described above were end-labelled using [γ-$^{32}$P]ATP (Dupont/NEN) and T4 Polynucleotide Kinase (Promega). Blots were prehybridized for 2 h at 42° C. in a hybridization buffer consisting of 5×SSC (where 1×SSC is 0.15 M NaCl/0.015 M sodium citrate) with 5×Denhardt's solution (where 1×Denhardt's is 0.02% Ficoll 400/0.02% polyvinyl-pyrrolidone/0.02% bovine serum albumin) and 0.02 mg/ml sonicated denatured salmon sperm DNA. Labelled oligonucleotide probes were then added at 1 pmol/ml and allowed to hybridize overnight at the same temperature. Blots were washed four times for 15 min in 0.5×SSC/0.1% (w/v) SDS at 45° C. and exposed to Fuji RX100 X-ray film.

Both oligonucleotide probes were found to hybridize to the same region of genomic DNA. A Bam III/Hin dIII fragment of 4.5 kb was selected for cloning. The vector used was pBluescript SK+ (Stratagene, Cambridge, UK). Genomic DNA was digested with Bam HI and Hin dIII and DNA fragments of 4 to 5 kb were eluted from agarose gels using the US Bioclean system (United States Biochemical Corporation, obtained through Amersham). Vector DNA was digested with the same enzymes, and vector and insert DNA were ligated using T4 DNA Ligase (Promega or Gibco/BRL). Electrocompetent *Escherichia coli* JM109 (obtained from Promega) was transformed with the ligation mixture by electroporation using a Bio-Rad Gene Pulser (Bio-Rad, Hemel Hempstead, Herts., UK). DNA from ampicillin-resistant transformants was transferred to Hybond-N+ membrane (Amersham) by colony blotting according to the manufacturer's protocol. Blots were screened using radiolabelled oligonucleotide probes as described above.

Figure 1:
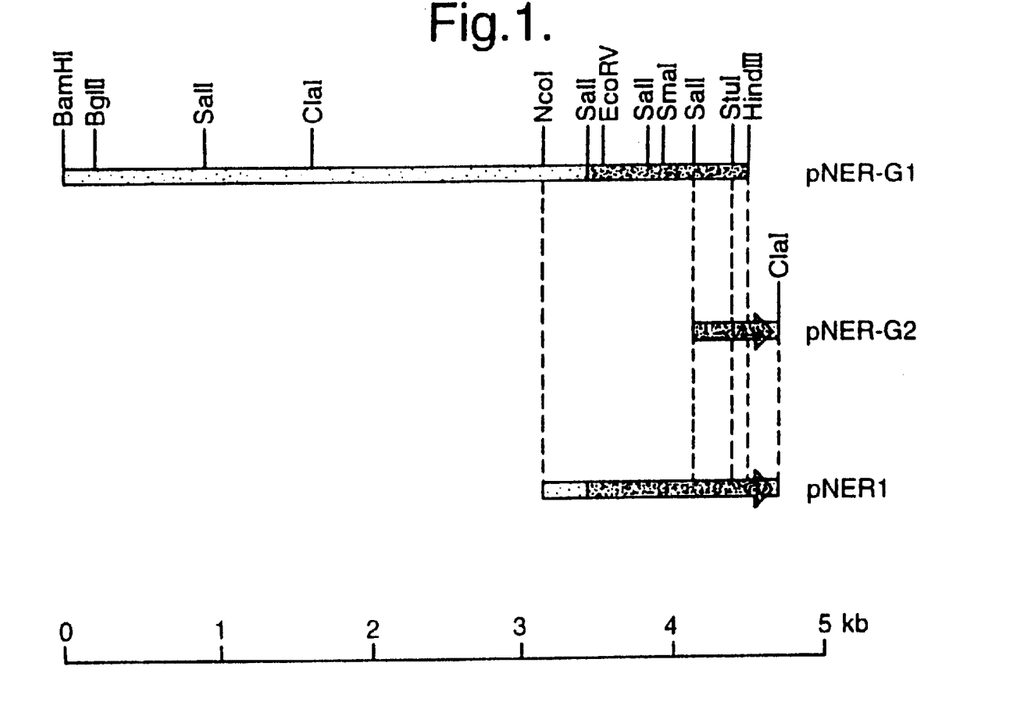
FIG. 1 shows an alignment of the DNA inserts in pNER-G1, pNER-G2 and pNER 1.

One clone, designated PNER-G1, was found to contain a 4.5 kb insert which hybridized to both probes. DNA sequencing demonstrated the presence of DNA encoding the N-terminal sequence of PETN reductase but showed that the Hin dIII site fell within the open reading frame so that the 3' end of the gene was missing FIG. 1). A further oligonucleotide probe, GACGCCGTGGCCTTTGGCCGTGAC (SEQ ID NO: 5), was designed based on the DNA sequence near the Hin DIII site, and was used to screen various restriction digests of genomic DNA as described above in order to locate the missing region. Hybridization with this probe was at 50° C. and blots were washed at 55° C., twice for 15 min with 1×SSC/0.1% (w/v) SDS and twice for 15 min with 0.2×SSC/0.1% (w/v) SDS. A Sal I/Cla I fragment of 0.5 kb was selected for cloning and was cloned as described above. This clone was designated pNER-G2. The regions of PNER-G1 and pNER-G2 bearing the onr gene were ligated together in pBluescript SK+ to create an Nco 1/Cla I insert of 1.5 kb bearing the entire onr gene. This construct was designated pNER1 (FIG. 1). Cell extracts from overnight cultures of *E. coli* JM109/pNER1 grown in a rich medium were prepared and assayed for PETN reductase activity. PETN reductase appeared to for m approximately 15% of soluble protein.

Figure 2:
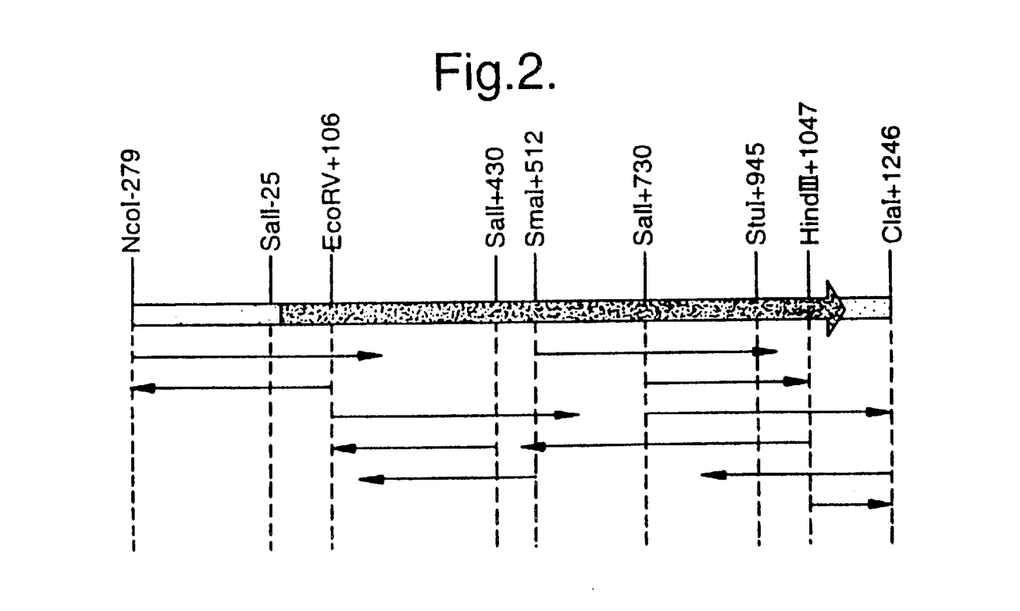
FIG. 2 demonstrates in schematic manner the stategy used for sequencing onr and flanking DNA.

Fragments of DNA from the region encoding PETN reductase were subcloned from pNER-G1, pNER-G2 and PNER1 in the vector pbluescript SK+ and sequenced using primers based on vector sequence. The sequencing strategy used is shown in FIG. 2. DNA for sequencing was prepared using the Qiagen Plasmid Mini Kit (Qiagen Ltd., Dorking, Surrey, UK). DNA sequencing was peformed by the DNA Sequencing Facility, Cambridge Centre for Molecular Recognition, Department of Biochemistry, University of Cambridge using a Pharmacia ALF DNA sequencer (Pharmacia Biotech, St. Albans, UK). The nucleotide sequence of the onr gene and the deduced amino acid sequence of PETN reductase are shown in FIG. 3.

Considering FIG. 1 further, it will be noted that all inserts are in the multi-cloning site of the vector pBlueseript SK+ (Stratagene). The dark arrow indicates the position of the onr gene encoding PETN reductase. The insert of pNER1 was prepared by ligating together the Nco 1/Stu I region of pNER-GI with the Stu I/Cla I region of pNER-G2. In pNER1 the Nco 1/Cla I fragment is inserted between the Bam HI and Cla I sites of the multi-cloning site of pBluescript SK+.

With particular reference to FIG. 2, subclones were prepared in pBluescript SK+ and sequenced using primers based on vector sequence. Arrows indicate sequencing reactions. The dark arrow indicates the coding region. The positions of restriction sites used in sequencing are numbered, with 1 being the A of the ATG initiating the coding region.

In FIG. 3, nucleotides are numbered with 1 being the A of the ATG initiating the coding region. A putative ribosome-binding site is indicated. It should be noted that the N-terminal amino acid sequence of PETN reductase shows that in *E cloacae* PB2 the initiating methionine is removed. The amino acid sequence is shown independently in FIG. 4.

Alternative ways of obtaining and cloning the gene will also be clear to the skilled person having knowledge of the gene sequence. For example suitable restriction enzymes may be employed to "cut" the DNA at restriction sites flanking the gene. Amplification of the gene may also be performed using PCR techniques employing suitably chosen primers flanking the gene.

EXAMPLE 5

Identfication of whole cell degradation products

Ethyl acetate extracts of supernatants from cultures grown with PETN contained PETN and three metabolites (as judged by HPLC). The metabolites were separated from PETN by TLC and found to have lower $R_f$ values (0.64, 0.53 and 0.23) than PETN ($R_f$ 0.81), indicating that the unknown metabolites were more polar than PETN.

The identity of the unknown metabolites was investigated using electron impact (EI) mass spectrometry. The EI mass spectrum of metabolite I revealed a molecular ion of m/z 227 which is consistent with the empirical formula $C_5H_{10}N_2O_8$. The mass spectrum contained a fragment ion at m/z 209. It is thought that this metabolite is pentaerythritol dinitrate (2,2-bisf(nitrooxy)methyl]-1,3-propanediol), a denitration product of PETN.

The EI mass spectrum of metabolite 2 revealed a molecular ion of m/z 224 which corresponds to the empirical formula $C_5H_8N_2O_8$. The mass spectrum contained fragment ions at m/z 207, 170, 141, 99, 76, 74, 158, 46 and 44. This is believed to represent 3-hydroxy-2,2-bis[(nitrooxy)methyl]propanal.

The EI mass spectrum of metabolite 3 revealed a molecular ion of m/z 222 which corresponds to the empirical formula $C_5H_6N_2O_8$. The mass spectrum contained fragment ions at m/z 208, 177 and 91. This is believed to represent 2,2-bis[(nitrooxy)methyl]-propanedial. The proposed structures for these metabolites are as follows:

The identity of Metabolite 1 was further investigated using $^1$H NMR at 400 mhz. The $^1$H NMR spectrum of pure PETN gave a single peak at 4.77 ppm which corresponds to the four equivalent methylene groups in PETN, whilst the $^1$H NMR spectrum of the unknown metabolite gave two separate peaks at 4.77 and 2.08 ppm. It is believed that the peak at 2.08 ppm corresponds to the methylene groups attached to the hydroxyl group in the proposed structural formula.

The (EI) mass spectroscopy and $^1$H NMR analysis of the unknown metabolites formed during PETN degradation by the bacterium suggest that at least two nitrogen atoms were used per PETN molecule; these metabolites provide no evidence for the removal of a third nitrate group.

EXAMPLE 6

Identification of the reaction products of PETN reductase

Following treatment of PETN with purified PETN reductase and NADPH, an ethyl acetate extract of the reaction mixture contained PETN and two metabolites (as judged by HPLC). The metabolites were separated from PETN by TLC and found to have lower $R_f$ values (0.78 and 0.64) than PETN ($R_f$ 0.8 1).

The identity of the unknown metabolites was investigated using (EI) mass spectrometry. The EI mass spectrum of metabolite A revealed a molecular ion of m/z 271 which corresponds to the empirical formula $C_5H_9N_3O_{10}$. The mass spectrum contained fragment ions at m/z 239 and 207. This is believed to represent pentaerythritol trinitrate. The EI mass spectrum and Rf value of metabolite B were identical to those of Metabolite I isolated from culture supenatant (see Example 2). This metabolite was identified as pentaerythritol dinitrate (PEDN). It therefore appears that PETN reductase reductively liberates nitrite from PETN to form pentaerythritol trinitrate and then PEDN, which is not a substrate for this enzyme. The presence of aldehydes formed from these alcohols in culture supernatants (Example 2) suggests subsequent dehydrogenase activity by another enzyme.

The specific activity of PETN reductase in crude extract was approximately 0.32 U/mg, equivalent to 9.7 mmol PETN(g soluble protein)$^{-1}$h$^{-1}$ assuming complete conversion of PETN to PEDN. This is probably sufficient to account for the observed specific degradation rate of PETN by growing cells of 1.03 mmol PETN (g protein)$^{-1}$h$^{-1}$.

EXAMPLE 7

Use of PETN reductase enzyme as a colorimetric detector for PETN

1. Methodology

This relies on the action of PETN reductase on PETN to produce nitrite which is then monitored by use of a Griess reagent. There was added to a series of uncontaminated soil samples (John Innes No. 2, 1 g in each case) placed in clean glass boiling tubes, known concentrations of PETN (from 1 to 500 μg) in HPLC acetone. Each of the samples was nixed thoroughly, placed in a vacuum oven and dried for 1 hour at room temperature.

These deliberately contaminated soil samples together with other soil samples (1 g) collected from ground which had been contaminated with either PETN or RDX/TNT mixtures were then each treated with 1.5 ml acetone per g of soil sample and shaken for 10 min. The soil was then allowed to settle under gravity after which 25 μl aliquots of the liquid were taken and added to 5ml Pyrex tubes containing a mixture of 12.8 μl of 7 mg/ml PETN reductase, 2 μl of 20 mM NADPH (enzyme cofactor) and 220.2 μl of 50 mM phosphate buffered saline. Each sample was mixed and then incubated for 10 min at room temperature. 200 μl of 1% sulphanilamide in 2.5% hydrochloric acid was then added to each tube (this forms a diazonium ion with nitrite) and incubated for a further 2 min prior to the addition of 40 μl of 0.5% N-(1-naphthyl)-ethylenediamine in water resulting in the generation of a purple-coloured product where PETN is present.

Figure 5:
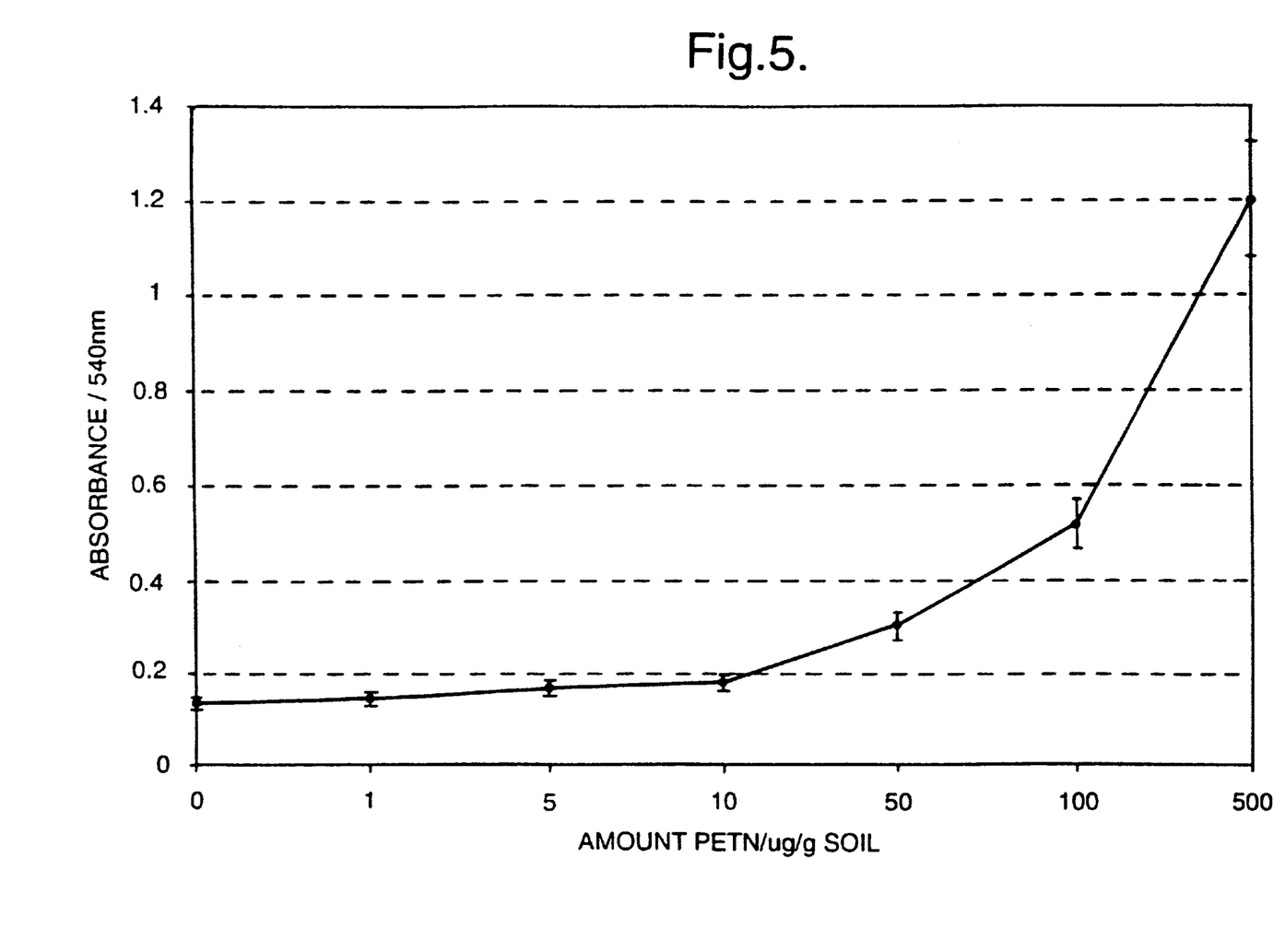
FIG. 5 is a PETN reductase assay standard curve for PETN-contaminated soils and to the following examples which further illustrate the invention but are not to be regarded as restrictive thereof.

200 μl of each sample was taken and placed in a microtiter plate and the absorbance of the sample then measured on a Ceres 900 UV HDi reader. From those samples derived from soil specimens having known PETN concentrations a standard curve of absorbance against PETN concentration in soil could be plotted (FIG. 5). Using this curve, optical densities obtained from samples of contaminated soils with unknown PETN content can be used to give an indication of the level of PETN contamination present within each sample.

Table 2 gives data obtained with a series of samples as indicated. These show that the assay described responds specifically to the levels of PETN in soil samples, that it does not give false positives in the absence of PETN or the presence of other explosives (RDX/TNT) and that it is dependent on the presence of the PETN reductase enyyme.

TABLE 2

| Sample characteristic | Sample No. | Absorbance at 540 nm | Amount of PETN/μg/g soil |
|---|---|---|---|
| no enzyme, 100 μg | 1 | 0.125 | 0 |
| spiked soil | 2 | 0.156 | 0 |
| uncontaminated | 3 | 0.137 | 0 |
| soil | 4 | 0.162 | 0 |
|  | 5 | 0.151 | 0 |
| TNT/RDX | 6 | 0.148 | 0 |
| contaminated | 7 | 0.131 | 0 |
| soil | 8 | 0.195 | 0 |
| PETN | 9 | 1.229 | 505 |
| contaminated | 10 | 0.482 | 95 |
| soils | 11 | 0.764 | 200 |
| PETN | 12 | 2.124 | 1200 |
| contaminated | 13 | 0.963 | 420 |
| soils | 14 | 0.805 | 280 |

We claim:

1. A PETN reductase enzyme which catalyses the removal of nitrite from PETN characterised in having the amino acid sequence as set forth in SEQ ID NO: 2.

2. A gene (designated onr) which encodes the PETN reductase enzyme of claim 1 characterised in having the nucleotide sequence as set forth in SEQ ID NO: 1.

3. A DNA molecule including the nucleotide sequence of the onr gene of claim 2.

4. PETN reductase enzyme which is encoded by the onr gene as claimed in claim 2.

5. A recombinant DNA vector containing the onr gene of claim 2.

6. A host cell transformed with the onr gene of claim 2.

7. A host cell transformed with a DNA molecule as claimed in claim 3.

8. A host cell transformed with a recombinant DNA vector as claimed in claim 5.

9. A method for the production of PETN reductase enzyme having the amino acid sequence as set forth in SEQ ID NO: 2 which comprises the steps of: transforming host cells with the onr gene of claim 2;

suitable culturing said transformed host cells; and extracting the PETN reductase enzyme from the growth medium or from the host cells after disruption thereof.

10. A method as claimed in claim 9 where the host cell is transformed by means of a recombinant DNA vector.

11. A method as claimed in claim 9 where the host cell is grown on a continuous basis with the PETN reductase enzyme being continuously extracted from the growth medium.

12. A method as claimed in claim 9 where the host cells in the culture are disrupted after an appropriate period of growth in order to extract the PETN reductase enzyme therefrom.

13. A method of detecting PETN in a sample, comprising subjecting the sample to a reaction involving the removal of nitrite from PETN, the reaction being carried out in the presence of NADPH and PETN reductase enzyme, having the amino acid sequence as set forth in SEQ ID NO: 2 until NADP and nitrite are produced, and detecting the occurrence of said reaction.

14. A method of detecting PETN in a sample, comprising subjecting the sample to a reaction involving the removal of nitrite from PETN, the reaction being carried out in the presence of NADPH and PETN reductase enzyme according to claim 4, until NADP and nitrite are produced, and detecting the occurrence of said reaction.

15. A method according to claim 13 or claim 14 wherein the NADP liberated in the reaction is detected.

16. A method according to claim 1 wherein NADP is detected by a bioluminescence test.

17. A method according to claim 16 wherein the bioluminescence test uses either bacterial or firefly luminescence.

18. A method according to claim 15 wherein NADP is detected amperometrically.

19. A method according to claim 13 or claim 15 wherein the nitrite liberated in the reaction is detected calorimetrically.

20. A method according to claim 19 wherein Griess Reagent is used for calorimetric detection of nitrite.

21. A method for the bioremedial treatment of an environment which is contaminated by PETN, GTN and/or EGDN comprising the steps of adding to the environment a quantity of PETN reductase enzyme according to claims 1, and maintaining the mixture under conditions appropriate for degradation of the contaminant by the PETN reductase enzyme so as to allow the PETN, GTN and/or EGDN present in the material to be consumed.

22. A method according to claim 21 wherein the material is a waste stream containing PETN, GTN and/or EGDN.

23. A method according to claim 21 wherein the material is a soil or ground sample contaminated with PETN, GTN and/or EGDN.

24. An *Enterobacter cloacae* bacterial strain referred to as "PB2" and deposited as NCIMB 40718, and mutants thereof capable of producing enzymic activity which degrades PETN in the presence of NADPH.

25. A process of producing a PETN reductase enzyme according to claim 1, which comprises culturing the Enterobacter cloacae sp NCIMB 40718, or a mutant thereof, in the presence of PETN as nitrogen source, at a temperature of from 20 to 40° C., disrupting the cells and recovering the PETN reductase enzyme from the disrupted cells.

26. A method for the bioremedial treatment of a PETN contaminated environment comprising the step of inoculating the environment with a sample of the bacterial isolate of *Enterobacter cloacae* as defined in claim 24 and allowing the isolate to consume the PETN present in the environment.

27. A method according to claim 26 wherein the environment is a waste stream containing PETN.

28. A method according to claim 26 wherein the environment is a soil or ground sample contaminated with PETN.

29. A method for producing pentaerythritol di- and trinitrates comprising reacting PETN with the PETN reductase enzyme of claim 1.

\* \* \* \* \*

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1531 base pairs
      (B) TYPE: nucleic acid
      (C) STRANDEDNESS: single
      (D) TOPOLOGY: linear    (ii) MOLECULE TYPE: cDNA    (ix) FEATURE:

(A) NAME/KEY: CDS
(B) LOCATION: 281..1375

(xi) SEQUENCE DESCRIPTION: SEQ ID NO:1:

```
CCATGGATAA AGGAGCCAGC GGCGTGATTG CCCTGTTGGC TCAGGCGCTG GAGAGCGGGC        60

GCAATGAAAA AACGCTCTCC TTCTCCGGCG ATCCGCTCAC GCAGGCACAG GTGCTCTATT       120

CCCTCTGGTT AGGCGCCAAC CTGCAAGCAA AAATGTCTCG CAGCGCCGTG CCGCTCGAAA       180

GCGCGCTGGC GCATGTGAAA AACTGTATTA CCGCGCCTGG CGTGTAGCCG GCGTTTTTAT       240

TTACCCTTTT ACTAGTCGAC TGGTCTACTC AGGAGCCGTT ATG TCC GCT GAA AAG        295
                                              Met Ser Ala Glu Lys
                                                1               5

CTG TTT ACC CCA CTG AAA GTG GGT GCC GTT ACT GCC CCA AAC CGC GTG        343
Leu Phe Thr Pro Leu Lys Val Gly Ala Val Thr Ala Pro Asn Arg Val
             10                  15                  20

TTT ATG GCC CCA CTT ACC CGT CTG CGC AGC ATC GAG CCG GGC GAT ATC        391
Phe Met Ala Pro Leu Thr Arg Leu Arg Ser Ile Glu Pro Gly Asp Ile
         25                  30                  35

CCA ACG CCA TTG ATG GGT GAG TAT TAC CGC CAG CGC GCC AGC GCG GGC        439
Pro Thr Pro Leu Met Gly Glu Tyr Tyr Arg Gln Arg Ala Ser Ala Gly
     40                  45                  50

CTG ATT ATC TCC GAA GCC ACG CAG ATT TCT GCT CAG GCA AAA GGC TAC        487
Leu Ile Ile Ser Glu Ala Thr Gln Ile Ser Ala Gln Ala Lys Gly Tyr
 55                  60                  65

GCC GGT GCA CCG GGT CTG CAC AGC CCG GAA CAG ATC GCC GCG TGG AAA        535
Ala Gly Ala Pro Gly Leu His Ser Pro Glu Gln Ile Ala Ala Trp Lys
 70                  75                  80                  85

AAA ATC ACC GCA GGC GTG CAT GCT GAA GAT GGC CGT ATT GCG GTT CAG        583
Lys Ile Thr Ala Gly Val His Ala Glu Asp Gly Arg Ile Ala Val Gln
             90                  95                 100

CTG TGG CAC ACC GGT CGT ATC TCA CAC AGC AGC ATC CAG CCT GGC GGT        631
Leu Trp His Thr Gly Arg Ile Ser His Ser Ser Ile Gln Pro Gly Gly
            105                 110                 115

CAG GCG CCG GTT TCT GCC TCT GCC CTG AAC GCC AAT ACC CGC ACT TCC        679
Gln Ala Pro Val Ser Ala Ser Ala Leu Asn Ala Asn Thr Arg Thr Ser
        120                 125                 130

CTG CGC GAT GAA AAC GGT AAT GCG ATC CGC GTC GAC ACC ACC ACG CCA        727
Leu Arg Asp Glu Asn Gly Asn Ala Ile Arg Val Asp Thr Thr Thr Pro
    135                 140                 145

CGC GCG CTG GAG CTG GAC GAG ATC CCG GGT ATC GTG AAT GAT TTC CGT        775
Arg Ala Leu Glu Leu Asp Glu Ile Pro Gly Ile Val Asn Asp Phe Arg
150                 155                 160                 165

CAG GCC GTC GCC AAC GCC CGG GAA GCG GGC TTC GAC CTG GTT GAG CTT        823
Gln Ala Val Ala Asn Ala Arg Glu Ala Gly Phe Asp Leu Val Glu Leu
                170                 175                 180

CAC TCT GCG CAC GGT TAC CTG CTG CAT CAG TTC CTG TCC CCG TCT TCC        871
His Ser Ala His Gly Tyr Leu Leu His Gln Phe Leu Ser Pro Ser Ser
            185                 190                 195

AAC CAG CGT ACC GAC CAG TAC GGC GGC AGC GTT GAA AAC CGC GCG CGT        919
Asn Gln Arg Thr Asp Gln Tyr Gly Gly Ser Val Glu Asn Arg Ala Arg
        200                 205                 210

CTG GTG CTT GAA GTG GTG GAT GCT GTC TGT AAT GAG TGG AGC GCA GAC        967
Leu Val Leu Glu Val Val Asp Ala Val Cys Asn Glu Trp Ser Ala Asp
    215                 220                 225

CGC ATT GGT ATT CGT GTC TCC CCG ATC GGT ACT TTC CAG AAC GTC GAC       1015
Arg Ile Gly Ile Arg Val Ser Pro Ile Gly Thr Phe Gln Asn Val Asp
230                 235                 240                 245

AAC GGT CCG AAC GAA GAA GCA GAC GCG CTG TAT CTG ATT GAA GAG CTG       1063
Asn Gly Pro Asn Glu Glu Ala Asp Ala Leu Tyr Leu Ile Glu Glu Leu
                250                 255                 260
```

```
GCG AAA CGC GGT ATC GCC TAT CTG CAC ATG TCC GAG ACG GAC TTG GCA       1111
Ala Lys Arg Gly Ile Ala Tyr Leu His Met Ser Glu Thr Asp Leu Ala
            265                 270                 275

GGC GGC AAG CCT TAC AGT GAA GCC TTC CGT CAG AAA GTG CGC GAG CGC       1159
Gly Gly Lys Pro Tyr Ser Glu Ala Phe Arg Gln Lys Val Arg Glu Arg
            280                 285                 290

TTC CAC GGC GTG ATT ATC GGG GCG GGT GCG TAT ACG GCA GAA AAA GCC       1207
Phe His Gly Val Ile Ile Gly Ala Gly Ala Tyr Thr Ala Glu Lys Ala
            295                 300                 305

GAG GAT TTG ATC GGT AAA GGC CTG ATC GAC GCC GTG GCC TTT GGC CGT       1255
Glu Asp Leu Ile Gly Lys Gly Leu Ile Asp Ala Val Ala Phe Gly Arg
310                 315                 320                 325

GAC TAC ATT GCT AAC CCG GAT CTG GTT GCC CGT TTG CAG AAA AAA GCC       1303
Asp Tyr Ile Ala Asn Pro Asp Leu Val Ala Arg Leu Gln Lys Lys Ala
                330                 335                 340

GAA CTG AAC CCG CAG CGT CCT GAA AGC TTC TAT GGC GGC GGC GCG GAA       1351
Glu Leu Asn Pro Gln Arg Pro Glu Ser Phe Tyr Gly Gly Gly Ala Glu
                345                 350                 355

GGT TAT ACC GAC TAC CCT TCA CTG TAATCCCGCT TTGTACATTG ATAGCGGCGA      1405
Gly Tyr Thr Asp Tyr Pro Ser Leu
            360                 365

CCTTTCGCCG CTATACTAAA ACATCGTTTC TGTTCAAAAA GATAATCCAT TCGACTGGTT    1465

AATGAGGAAA TTATGCGCCT ACTTCACACC ATGCTGCGCG TTGGCGACCT GCAACGTTCC    1525

ATCGAT                                                               1531

(2) INFORMATION FOR SEQ ID NO:2:

(i) SEQUENCE CHARACTERISTICS:
        (A) LENGTH: 365 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Ala Glu Lys Leu Phe Thr Pro Leu Lys Val Gly Ala Val Thr
1               5                   10                  15

Ala Pro Asn Arg Val Phe Met Ala Pro Leu Thr Arg Leu Arg Ser Ile
                20                  25                  30

Glu Pro Gly Asp Ile Pro Thr Pro Leu Met Gly Glu Tyr Tyr Arg Gln
            35                  40                  45

Arg Ala Ser Ala Gly Leu Ile Ile Ser Glu Ala Thr Gln Ile Ser Ala
        50                  55                  60

Gln Ala Lys Gly Tyr Ala Gly Ala Pro Gly Leu His Ser Pro Glu Gln
65                  70                  75                  80

Ile Ala Ala Trp Lys Lys Ile Thr Ala Gly Val His Ala Glu Asp Gly
                85                  90                  95

Arg Ile Ala Val Gln Leu Trp His Thr Gly Arg Ile Ser His Ser Ser
            100                 105                 110

Ile Gln Pro Gly Gly Gln Ala Pro Val Ser Ala Ser Ala Leu Asn Ala
        115                 120                 125

Asn Thr Arg Thr Ser Leu Arg Asp Glu Asn Gly Asn Ala Ile Arg Val
    130                 135                 140

Asp Thr Thr Thr Pro Arg Ala Leu Glu Leu Asp Glu Ile Pro Gly Ile
145                 150                 155                 160

Val Asn Asp Phe Arg Gln Ala Val Ala Asn Ala Arg Glu Ala Gly Phe
                165                 170                 175
```

```
Asp Leu Val Glu Leu His Ser Ala His Gly Tyr Leu Leu His Gln Phe
        180                 185                 190

Leu Ser Pro Ser Ser Asn Gln Arg Thr Asp Gln Tyr Gly Gly Ser Val
        195                 200                 205

Glu Asn Arg Ala Arg Leu Val Leu Glu Val Val Asp Ala Val Cys Asn
        210                 215                 220

Glu Trp Ser Ala Asp Arg Ile Gly Ile Arg Val Ser Pro Ile Gly Thr
225                 230                 235                 240

Phe Gln Asn Val Asp Asn Gly Pro Asn Glu Glu Ala Asp Ala Leu Tyr
                245                 250                 255

Leu Ile Glu Glu Leu Ala Lys Arg Gly Ile Ala Tyr Leu His Met Ser
            260                 265                 270

Glu Thr Asp Leu Ala Gly Gly Lys Pro Tyr Ser Glu Ala Phe Arg Gln
        275                 280                 285

Lys Val Arg Glu Arg Phe His Gly Val Ile Ile Gly Ala Gly Ala Tyr
        290                 295                 300

Thr Ala Glu Lys Ala Glu Asp Leu Ile Gly Lys Gly Leu Ile Asp Ala
305                 310                 315                 320

Val Ala Phe Gly Arg Asp Tyr Ile Ala Asn Pro Asp Leu Val Ala Arg
                325                 330                 335

Leu Gln Lys Lys Ala Glu Leu Asn Pro Gln Arg Pro Glu Ser Phe Tyr
            340                 345                 350

Gly Gly Gly Ala Glu Gly Tyr Thr Asp Tyr Pro Ser Leu
        355                 360                 365

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:3:

ACTTTSAGSG GSGTGAASAG TTTTTCSGC                                    29

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:4:

GTSAGSGGSG CCATGAASAC SCGGTT                                       26

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"
```

(xi) SEQUENCE DESCRIPTION: SEQ ID NO:5:

GACGCCGTGG CCTTTGGCCG TGAC                                    24